United States Patent
Carlyon

(10) Patent No.: US 8,348,893 B2
(45) Date of Patent: Jan. 8, 2013

(54) LOCKING CLIP ASSEMBLY WITH SPRING-LOADED COLLAR

(75) Inventor: James L. Carlyon, Farmington, MO (US)

(73) Assignee: Covidien LP, Mansfield, MA (US)

( * ) Notice: Subject to any disclaimer, the term of this patent is extended or adjusted under 35 U.S.C. 154(b) by 1055 days.

(21) Appl. No.: 12/338,284

(22) Filed: Dec. 18, 2008

(65) Prior Publication Data

US 2009/0163861 A1 Jun. 25, 2009

Related U.S. Application Data

(60) Provisional application No. 61/008,481, filed on Dec. 20, 2007.

(51) Int. Cl.
*A61M 5/00* (2006.01)
*A61M 5/178* (2006.01)
*A61M 5/32* (2006.01)

(52) U.S. Cl. .................... 604/110; 604/164.08; 604/198

(58) Field of Classification Search .................. 604/110, 604/164.01, 164.08, 162, 163, 187, 192, 604/195–198, 171, 263
See application file for complete search history.

(56) References Cited

U.S. PATENT DOCUMENTS

| | | | |
|---|---|---|---|
| 1,115,561 A | 11/1914 | Northey | |
| 1,436,707 A | 11/1922 | Gaschke | |
| 1,518,531 A | 12/1924 | Lung | |
| 2,623,521 A | 12/1952 | Shaw | |
| 2,854,976 A | 10/1958 | Heydrich | |
| 3,308,821 A | 3/1967 | Shields | |
| 3,610,240 A | 10/1971 | Harautuneian | |
| 3,884,230 A | 5/1975 | Wulff | |
| 3,890,971 A | 6/1975 | Leeson et al. | |
| 3,904,033 A | 9/1975 | Haerr | |
| 3,976,070 A | 8/1976 | Dumont | |
| 3,977,400 A | 8/1976 | Moorehead | |
| 3,994,287 A | 11/1976 | Turp et al. | |
| 4,000,739 A | 1/1977 | Stevens | |
| 4,026,287 A | 5/1977 | Haller | |
| 4,139,009 A | 2/1979 | Alvarez | |
| 4,143,853 A | 3/1979 | Abramson | |
| 4,160,450 A | 7/1979 | Doherty | |
| 4,177,814 A | 12/1979 | Knepshield et al. | |
| 4,211,214 A | 7/1980 | Chikashige | |
| 4,258,713 A | 3/1981 | Wardlaw | |
| 4,261,357 A | 4/1981 | Kontos | |
| 4,266,543 A | 5/1981 | Blum | |
| 4,387,879 A | 6/1983 | Tauschinski | |
| 4,392,859 A | 7/1983 | Dent | |

(Continued)

FOREIGN PATENT DOCUMENTS

EP 0750915 1/1997

(Continued)

*Primary Examiner* — Nicholas Lucchesi
*Assistant Examiner* — Jenna Zhang
(74) *Attorney, Agent, or Firm* — Lisa E. Winsor

(57) ABSTRACT

A catheter assembly is disclosed which includes a cannula assembly, a locking clip assembly and a housing. The locking clip assembly includes a locking clip, a collar, and a biasing member. The locking clip has a first leg defining a trigger hole and a second leg defining a binding hole. The collar is positioned to engage the locking clip and the biasing member is positioned to urge the collar into engagement with the locking clip to urge the locking clip from a first orientation to a second orientation. In the second orientation, the binding hole is positioned to bind with the insertion needle to prevent retraction of the insertion needle.

21 Claims, 5 Drawing Sheets

U.S. PATENT DOCUMENTS

| | | |
|---|---|---|
| 4,424,833 A | 1/1984 | Spector et al. |
| 4,425,120 A | 1/1984 | Sampson et al. |
| 4,430,081 A | 2/1984 | Timmermans |
| 4,436,519 A | 3/1984 | O'Neill |
| 4,447,237 A | 5/1984 | Frisch et al. |
| 4,473,067 A | 9/1984 | Schiff |
| 4,475,548 A | 10/1984 | Muto |
| 4,482,348 A | 11/1984 | Dent |
| 4,512,766 A | 4/1985 | Vailancourt |
| 4,573,976 A | 3/1986 | Sampson et al. |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,631,057 A | 12/1986 | Mitchell |
| 4,634,432 A | 1/1987 | Kocak |
| 4,639,249 A | 1/1987 | Larson |
| 4,643,199 A | 2/1987 | Jennings, Jr. et al. |
| 4,643,200 A | 2/1987 | Jennings, Jr. et al. |
| 4,649,904 A | 3/1987 | Krauter et al. |
| 4,655,752 A | 4/1987 | Honkanen et al. |
| 4,664,654 A | 5/1987 | Strauss |
| 4,673,393 A | 6/1987 | Suzuki et al. |
| 4,676,783 A | 6/1987 | Jagger et al. |
| 4,681,567 A | 7/1987 | Masters et al. |
| 4,693,708 A | 9/1987 | Wanderer et al. |
| 4,695,274 A | 9/1987 | Fox |
| 4,705,511 A | 11/1987 | Kocak |
| 4,715,360 A | 12/1987 | Akui et al. |
| 4,722,725 A | 2/1988 | Sawyer et al. |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry et al. |
| 4,737,144 A | 4/1988 | Choksi |
| 4,738,663 A | 4/1988 | Bogan |
| 4,743,233 A | 5/1988 | Schneider |
| 4,747,831 A | 5/1988 | Kulli |
| 4,747,836 A | 5/1988 | Luther |
| 4,747,837 A | 5/1988 | Hauck |
| 4,752,290 A | 6/1988 | Schramm |
| 4,758,225 A | 7/1988 | Cox et al. |
| 4,762,516 A | 8/1988 | Luther et al. |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,781,693 A | 11/1988 | Martinez et al. |
| 4,790,827 A | 12/1988 | Haber et al. |
| 4,790,828 A | 12/1988 | Dombrowski et al. |
| 4,795,432 A | 1/1989 | Karczmer |
| 4,798,594 A | 1/1989 | Hillstead |
| 4,804,372 A | 2/1989 | Laico et al. |
| 4,809,679 A | 3/1989 | Shimonaka et al. |
| 4,810,248 A | 3/1989 | Masters et al. |
| 4,813,426 A | 3/1989 | Haber et al. |
| 4,816,022 A | 3/1989 | Poncy |
| 4,817,631 A | 4/1989 | Schnepp-Pesch et al. |
| 4,819,659 A | 4/1989 | Sitar |
| 4,820,275 A | 4/1989 | Haber et al. |
| 4,826,488 A | 5/1989 | Nelson et al. |
| 4,826,490 A | 5/1989 | Byrne et al. |
| 4,826,491 A | 5/1989 | Schramm |
| 4,834,718 A | 5/1989 | McDonald |
| 4,838,282 A | 6/1989 | Strasser et al. |
| 4,846,809 A | 7/1989 | Sims |
| 4,857,062 A | 8/1989 | Russell |
| 4,874,377 A | 10/1989 | Newgard et al. |
| 4,895,346 A | 1/1990 | Steigerwald |
| 4,895,565 A | 1/1990 | Hillstead |
| 4,900,307 A | 2/1990 | Kulli |
| 4,904,242 A | 2/1990 | Kulli |
| 4,909,793 A | 3/1990 | Vining et al. |
| 4,909,798 A | 3/1990 | Fleischhacker et al. |
| 4,911,694 A | 3/1990 | Dolan |
| 4,911,706 A | 3/1990 | Levitt |
| 4,917,668 A | 4/1990 | Haindl |
| 4,927,414 A | 5/1990 | Kulli |
| 4,929,234 A | 5/1990 | Chen |
| 4,929,241 A | 5/1990 | Kulli |
| 4,931,044 A | 6/1990 | Beiter |
| 4,932,633 A | 6/1990 | Johnson et al. |
| 4,935,010 A | 6/1990 | Cox et al. |
| 4,935,013 A | 6/1990 | Haber |
| 4,944,725 A | 7/1990 | McDonald |
| 4,950,250 A | 8/1990 | Haber et al. |
| 4,950,257 A | 8/1990 | Hibbs et al. |
| 4,952,207 A | 8/1990 | Lemieux |
| 4,955,866 A | 9/1990 | Corey |
| 4,960,412 A | 10/1990 | Fink |
| 4,964,854 A | 10/1990 | Luther |
| 4,966,587 A | 10/1990 | Baumgart |
| 4,978,344 A | 12/1990 | Dombrowski et al. |
| 4,994,041 A | 2/1991 | Dombrowski et al. |
| 5,000,745 A | 3/1991 | Guest et al. |
| 5,013,304 A | 5/1991 | Russell et al. |
| 5,049,136 A | 9/1991 | Johnson |
| 5,051,109 A | 9/1991 | Simon |
| 5,053,017 A | 10/1991 | Chamuel |
| 5,059,180 A | 10/1991 | McLees |
| 5,085,648 A | 2/1992 | Purdy et al. |
| 5,102,394 A | 4/1992 | Lasaitis et al. |
| 5,108,374 A | 4/1992 | Lemieux |
| 5,126,090 A | 6/1992 | Egolf et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,183,468 A | 2/1993 | McLees |
| 5,195,983 A | 3/1993 | Boese |
| 5,215,525 A | 6/1993 | Sturman |
| 5,215,528 A | 6/1993 | Purdy et al. |
| 5,279,591 A | 1/1994 | Simon |
| 5,312,359 A | 5/1994 | Wallace |
| 5,322,517 A | 6/1994 | Sircom et al. |
| 5,322,518 A | 6/1994 | Schneider et al. |
| 5,328,482 A | 7/1994 | Sircom et al. |
| 5,334,158 A | 8/1994 | McLees |
| 5,338,311 A | 8/1994 | Mahurkar |
| 5,344,408 A | 9/1994 | Partika |
| 5,348,544 A | 9/1994 | Sweeney et al. |
| 5,364,387 A | 11/1994 | Sweeney |
| 5,370,623 A | 12/1994 | Kreamer |
| 5,390,898 A | 2/1995 | Smedley et al. |
| 5,405,323 A | 4/1995 | Rogers et al. |
| 5,409,461 A | 4/1995 | Steinman |
| 5,411,486 A | 5/1995 | Zadini et al. |
| 5,417,659 A | 5/1995 | Gaba |
| 5,419,766 A | 5/1995 | Chang et al. |
| 5,423,766 A | 6/1995 | DiCesare |
| 5,425,718 A | 6/1995 | Tay et al. |
| 5,425,884 A | 6/1995 | Botz |
| 5,458,658 A | 10/1995 | Sircom |
| 5,466,223 A | 11/1995 | Bressler et al. |
| 5,501,675 A | 3/1996 | Erskine |
| 5,514,100 A | 5/1996 | Mahurkar |
| 5,533,974 A | 7/1996 | Gaba |
| 5,535,771 A | 7/1996 | Purdy et al. |
| 5,555,908 A | 9/1996 | Edwards et al. |
| 5,558,651 A | 9/1996 | Crawford et al. |
| 5,562,629 A * | 10/1996 | Haughton et al. ............ 604/158 |
| 5,562,633 A | 10/1996 | Wozencroft |
| 5,562,683 A | 10/1996 | Chan |
| 5,572,516 A | 11/1996 | Miya et al. |
| 5,573,510 A | 11/1996 | Isaacson |
| 5,584,809 A | 12/1996 | Gaba |
| 5,584,810 A | 12/1996 | Brimhall |
| 5,584,818 A | 12/1996 | Morrison |
| 5,599,310 A | 2/1997 | Bogert |
| 5,601,536 A | 2/1997 | Crawford et al. |
| 5,611,781 A | 3/1997 | Sircom et al. |
| 5,662,610 A | 9/1997 | Sircom |
| 5,672,161 A | 9/1997 | Allen et al. |
| 5,679,907 A | 10/1997 | Ruck |
| 5,685,862 A | 11/1997 | Mahurkar |
| 5,687,907 A | 11/1997 | Holden |

| Patent No. | Date | Inventor |
|---|---|---|
| 5,690,619 A | 11/1997 | Erskine |
| 5,693,022 A | 12/1997 | Haynes |
| 5,695,467 A | 12/1997 | Miyata et al. |
| 5,697,907 A * | 12/1997 | Gaba ............................ 604/110 |
| 5,700,249 A | 12/1997 | Jenkins |
| 5,700,250 A | 12/1997 | Erskine |
| 5,702,369 A | 12/1997 | Mercereau |
| 5,718,688 A | 2/1998 | Wozencroft |
| 5,735,827 A | 4/1998 | Adwers et al. |
| 5,738,144 A | 4/1998 | Rogers |
| 5,738,665 A | 4/1998 | Caizza et al. |
| 5,788,215 A | 8/1998 | Ryan |
| 5,806,551 A | 9/1998 | Meloul et al. |
| 5,806,831 A | 9/1998 | Paradis |
| 5,814,098 A | 9/1998 | Hinnenkamp et al. |
| 5,817,069 A | 10/1998 | Arnett |
| 5,836,921 A | 11/1998 | Mahurkar |
| 5,853,393 A | 12/1998 | Bogert |
| 5,865,806 A | 2/1999 | Howell |
| 5,879,337 A | 3/1999 | Kuracina et al. |
| 5,879,338 A | 3/1999 | Mahurkar |
| 5,882,337 A | 3/1999 | Bogert et al. |
| 5,891,105 A | 4/1999 | Mahurkar |
| 5,893,845 A | 4/1999 | Newby et al. |
| 5,910,130 A | 6/1999 | Caizza et al. |
| 5,911,705 A | 6/1999 | Howell |
| 5,928,162 A | 7/1999 | Giurtino et al. |
| 5,935,109 A | 8/1999 | Donnan |
| 5,947,930 A | 9/1999 | Schwemberger et al. |
| 5,954,313 A | 9/1999 | Ryan |
| 5,954,698 A | 9/1999 | Pike |
| 5,957,887 A | 9/1999 | Österlind et al. |
| 5,957,892 A | 9/1999 | Thorne |
| 5,967,490 A | 10/1999 | Pike |
| 5,967,698 A | 10/1999 | Pascoe |
| 5,980,488 A | 11/1999 | Thorne |
| 5,989,229 A | 11/1999 | Chiappetta |
| 6,001,080 A | 12/1999 | Kuracina et al. |
| 6,004,294 A | 12/1999 | Brimhall et al. |
| 6,068,011 A | 5/2000 | Paradis |
| 6,068,617 A | 5/2000 | Richmond |
| 6,083,202 A | 7/2000 | Smith |
| RE36,885 E | 9/2000 | Blecher et al. |
| 6,117,108 A | 9/2000 | Woehr et al. |
| 6,117,112 A | 9/2000 | Mahurkar |
| 6,132,401 A | 10/2000 | Van Der Meyden et al. |
| 6,171,284 B1 | 1/2001 | Kao et al. |
| 6,203,527 B1 | 3/2001 | Zadini et al. |
| 6,210,373 B1 | 4/2001 | Allmon |
| 6,221,047 B1 | 4/2001 | Greene et al. |
| 6,224,569 B1 | 5/2001 | Brimhall |
| 6,280,399 B1 | 8/2001 | Rossin et al. |
| 6,280,401 B1 | 8/2001 | Mahurkar |
| 6,280,419 B1 | 8/2001 | Vojtasek |
| 6,287,278 B1 | 9/2001 | Woehr et al. |
| 6,322,537 B1 | 11/2001 | Chang |
| 6,361,525 B2 | 3/2002 | Capes et al. |
| 6,379,333 B1 | 4/2002 | Brimhall et al. |
| 6,406,459 B1 | 6/2002 | Allmon |
| 6,409,701 B1 | 6/2002 | Cohn et al. |
| 6,443,927 B1 | 9/2002 | Cook |
| 6,443,929 B1 * | 9/2002 | Kuracina et al. ............ 604/192 |
| 6,485,468 B2 | 11/2002 | Vojtasek |
| 6,485,473 B1 | 11/2002 | Lynn |
| 6,500,129 B1 | 12/2002 | Mahurkar |
| 6,517,516 B1 | 2/2003 | Caizza |
| 6,537,259 B1 | 3/2003 | Niermann |
| 6,551,287 B2 | 4/2003 | Hollister et al. |
| 6,582,402 B1 | 6/2003 | Erskine |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,623,458 B2 | 9/2003 | Woehr et al. |
| 6,638,254 B2 | 10/2003 | Nakagami |
| 6,652,486 B2 | 11/2003 | Bialecki et al. |
| 6,652,490 B2 | 11/2003 | Howell |
| 6,663,592 B2 | 12/2003 | Rhad et al. |
| 6,673,047 B2 | 1/2004 | Crawford et al. |
| 6,682,510 B2 | 1/2004 | Niermann |
| 6,689,102 B2 | 2/2004 | Greene |
| 6,692,471 B2 | 2/2004 | Boudreaux |
| 6,699,221 B2 | 3/2004 | Vaillancourt |
| 6,740,063 B2 | 5/2004 | Lynn |
| 6,749,588 B1 | 6/2004 | Howell et al. |
| 6,761,704 B2 | 7/2004 | Crawford |
| 6,761,706 B2 | 7/2004 | Vaillancourt |
| 6,767,336 B1 | 7/2004 | Kaplan |
| 6,796,962 B2 | 9/2004 | Ferguson et al. |
| 6,802,490 B2 | 10/2004 | Leinsing et al. |
| 6,832,992 B2 | 12/2004 | Wilkinson |
| 6,855,128 B2 | 2/2005 | Swenson |
| 6,855,130 B2 | 2/2005 | Saulenas et al. |
| 6,902,546 B2 | 6/2005 | Ferguson |
| 6,916,311 B2 | 7/2005 | Vojtasek |
| 6,936,036 B2 | 8/2005 | Wilkinson et al. |
| 6,984,213 B2 * | 1/2006 | Horner et al. ............... 600/564 |
| 7,004,927 B2 | 2/2006 | Ferguson et al. |
| 2001/0018573 A1 | 8/2001 | Woehr |
| 2001/0027298 A1 | 10/2001 | Vojtasek |
| 2001/0029356 A1 | 10/2001 | Vojtasek |
| 2002/0151850 A1 | 10/2002 | Ferguson et al. |
| 2002/0169418 A1 | 11/2002 | Menzi et al. |
| 2002/0193745 A1 | 12/2002 | Ferguson |
| 2003/0144627 A1 | 7/2003 | Woehr et al. |
| 2003/0195471 A1 | 10/2003 | Woehr et al. |
| 2003/0220617 A1 | 11/2003 | Dickerson |
| 2004/0078003 A1 * | 4/2004 | Smith et al. ............. 604/164.08 |
| 2004/0092889 A1 | 5/2004 | Ferguson et al. |
| 2004/0133167 A1 | 7/2004 | Ferguson et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0059936 A1 * | 3/2005 | Fiser et al. .................... 604/263 |
| 2005/0059937 A1 | 3/2005 | Ferguson |
| 2005/0070855 A1 | 3/2005 | Ferguson et al. |
| 2005/0096592 A1 * | 5/2005 | Carlyon et al. ............... 604/110 |

FOREIGN PATENT DOCUMENTS

| | | |
|---|---|---|
| EP | 1112754 | 2/2005 |
| WO | W09622800 | 8/1996 |
| WO | W09742989 | 11/1997 |
| WO | WO2005042073 | 5/2005 |

* cited by examiner

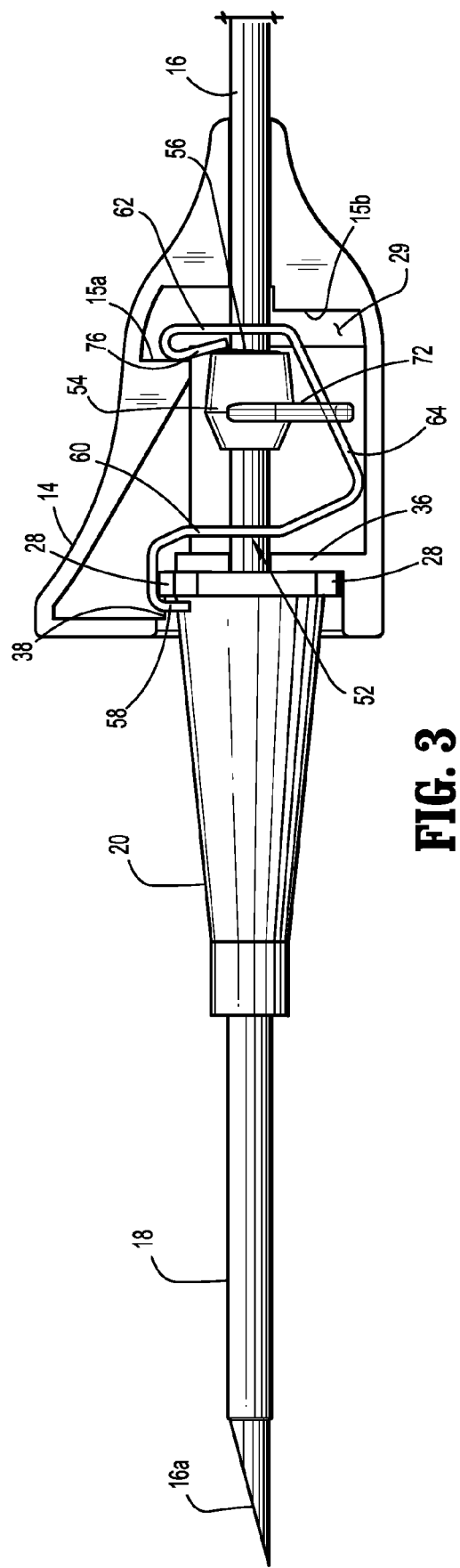
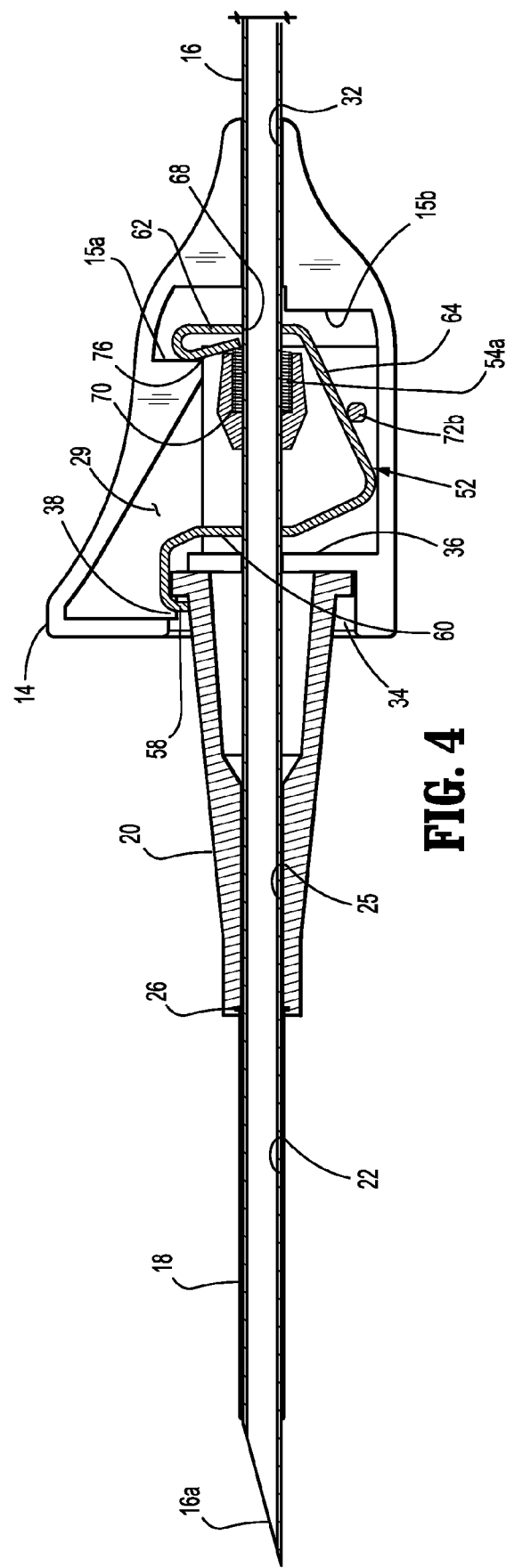

LOCKING CLIP ASSEMBLY WITH SPRING-LOADED COLLAR

CROSS-REFERENCE TO RELATED APPLICATIONS

The present application claims the benefit of and priority to U.S. Provisional Patent Application No. 61/008,481, filed on Dec. 20, 2007, which is incorporated herein by reference in its entirety.

BACKGROUND

1. Technical Field

The present disclosure relates to safety devices for shielding medical needles. More particularly, the present disclosure relates to a needle locking assembly for shielding an insertion needle of an intravenous (I.V.) catheter assembly.

2. Background of Related Art

Safety devices for shielding needles of medical devices are well known in the art. Such devices minimize the risks associated with inadvertent needle stick injuries which subject doctors, nurses and medical personnel to exposure to HIV, hepatitis and other serious blood-borne pathogens. I.V. catheter assemblies are also known in the art and typically include a catheter which is dimensioned to be positioned into a patient's vasculature and a needle having a sharp tip which is provided to facilitate placement of the catheter into the patient's vasculature. In use, after placement of the catheter, the needle is separated from the catheter and disposed of safely. One problem associated with the use of I.V. catheters is the risk to medical personnel of needle stick injury during disposal of the needle after separation of the needle from the catheter. To minimize the risks to medical personnel during needle disposal, the use of locking clip assemblies which engage the needle to confine the needle tip within a housing have become well known.

Typically, current locking clip assemblies include a spring clip which is used in combination with an insertion needle having an area of increased diameter. The area of increased diameter may be formed by deforming the needle or securing, such as by welding, an annular ring to the needle. The area of increased diameter creates a positive stop for preventing the needle from separating from the locking clip. Such locking clip devices, due to the increased diameter of the insertion needle, may cause discomfort to a patient. In addition, where an annular ring is secured to the insertion needle, the risk exists that the annular ring will become detached from the insertion needle and occlude flow within a patient's vasculature.

Other known locking clip devices include a spring clip which applies a spring force directly to the insertion needle shaft to cause rotation of the spring clip into a binding orientation with the insertion needle. See U.S. patent application Ser. Nos. 10/698,869 and 10/585,987. Such a spring force applied to the insertion needle by the spring clip may create a high drag force on the insertion needle as it is separated from the catheter assembly making it difficult for a clinician to remove the insertion needle from the catheter assembly.

Accordingly, a need exists in the medical arts for an I.V. catheter assembly which includes a locking clip device which does not suffer from the drawbacks identified above, but is easy to manufacture and functions reliably.

SUMMARY

A catheter assembly is disclosed which includes a cannula assembly, a locking clip assembly and a housing. The cannula assembly includes a cannula and a cannula hub. The locking clip assembly includes a locking clip, a collar, and a biasing member. The locking clip has a first leg defining a trigger hole and a second leg defining a binding hole. The collar is positioned to engage the locking clip and the biasing member is positioned to urge the collar into engagement with the locking clip to urge the locking clip from a first orientation to a second orientation. The housing defines a chamber dimensioned to receive the locking clip assembly. An insertion needle is movable from an advanced position to a retracted position, wherein in the advanced position, the insertion needle extends through the housing, the binding and trigger holes of the locking clip and the cannula assembly such that a sharp distal end of the insertion needle extends from a distal end of the cannula and the locking clip is retained in its first orientation. In the retracted position, the distal end of the insertion needle is withdrawn through the cannula assembly and the trigger hole such that the collar and biasing member urge the locking clip to the second orientation, wherein the binding hole is positioned to bind with the insertion needle to prevent retraction of the insertion needle. In one embodiment, the biasing member includes a coil spring.

The collar may define a bore such that the collar is slidably positioned about the insertion needle. The collar may also include a cantilevered arm which is positioned to engage the locking clip. In one embodiment, the collar is slidably supported on the insertion needle between the first and second legs of the locking clip and the biasing member is positioned about the insertion needle between a proximal end of the collar and a distal surface of the second leg of the locking clip.

The locking clip may have an angled portion interconnecting the first and second legs of the locking clip such that the arm of the collar engages the angled portion of the locking clip to urge the locking clip towards its second orientation. In one embodiment, the arm includes a vertical portion which extends downwardly from the collar and a horizontal portion which extends across the angled portion of the locking clip.

In one embodiment, the housing defines an annular recess dimensioned to receive a proximal end of the cannula hub. The proximal end of the cannula hub includes a coupling member which may be a luer-type connector having at least one radially extending tab. The locking clip may include a hook portion which is configured to engage the coupling member of the cannula hub when the locking clip is in its first orientation to releasably secure the cannula hub to the housing. In one embodiment, the housing includes a partition wall separating the annular recess from the chamber. The partition wall defines a cutout dimensioned to receive the hook portion of the locking clip.

A locking clip assembly is also provided which includes a housing, a locking clip, a collar and a biasing member. The housing defines a chamber and proximal and distal openings. The proximal and distal openings are dimensioned to receive an insertion needle of a catheter assembly. The locking clip has a first leg defining a trigger hole and a second leg defining a binding hole. The trigger hole and the binding hole are dimensioned to slidably receive an insertion needle of a catheter assembly. The locking clip is movably supported within the chamber of the housing from a first orientation to a second orientation. The collar is positioned to engage the locking clip and the biasing member is positioned to urge the collar into engagement with the locking clip to urge the locking clip from its first orientation to its second orientation. In second orientation of the locking clip, the binding hole of the locking clip is positioned to bind against an insertion needle of a catheter assembly.

BRIEF DESCRIPTION OF THE DRAWINGS

Various embodiments of the presently disclosed locking clip assembly with spring-loaded collar are disclosed herein with reference to the drawings, wherein:

FIG. 3 is a side view of the I.V. catheter assembly shown in FIG. 1 with a housing half-section removed;

FIG. 4 is a side cross-sectional view of the I.V. catheter assembly shown in FIG. 1;

DETAILED DESCRIPTION OF EMBODIMENTS

Figure 1:
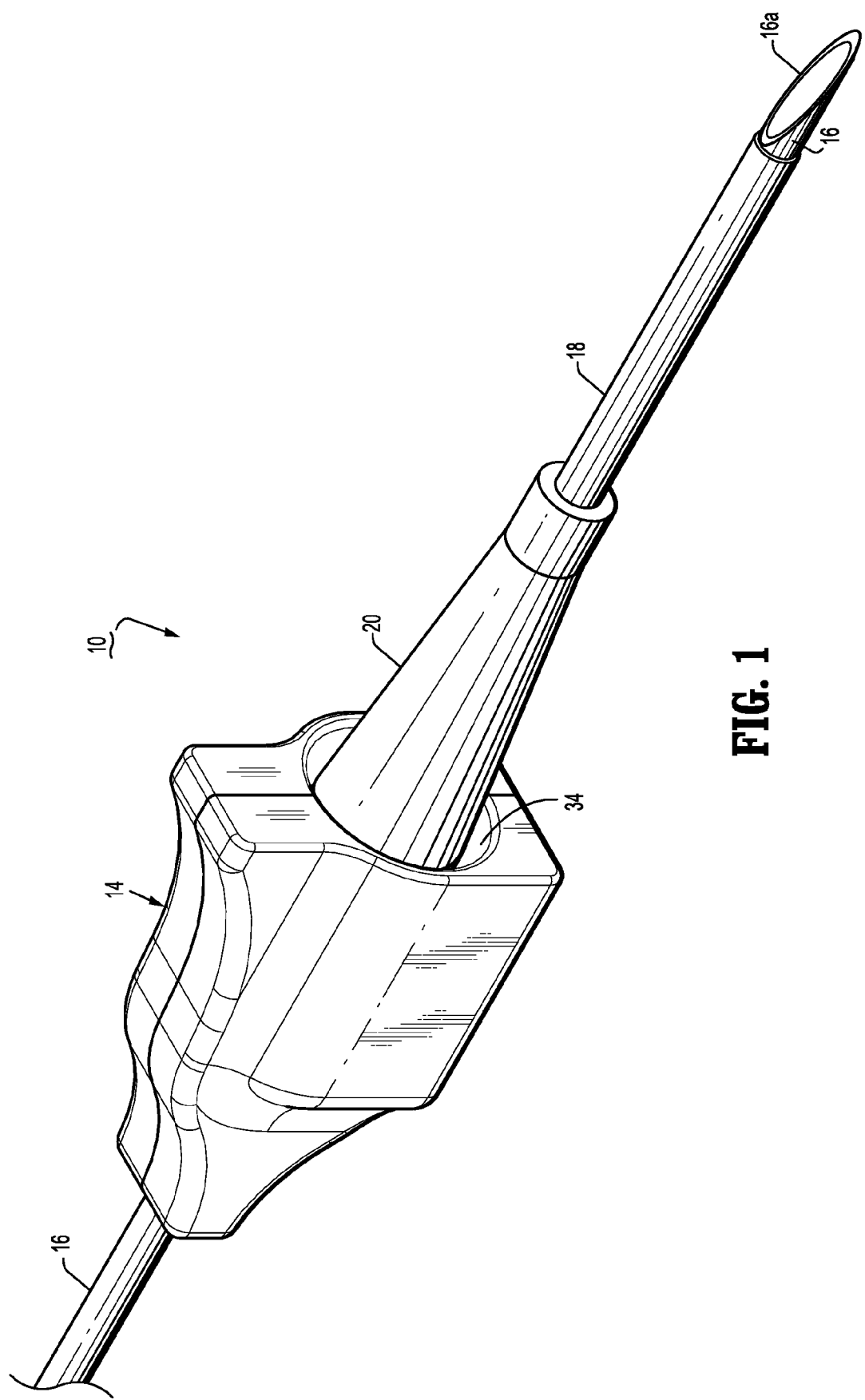
FIG. 1 is a side perspective view of an I.V. catheter assembly incorporating one embodiment of the presently disclosed locking clip assembly with an insertion needle in its advanced position.
Figure 2:
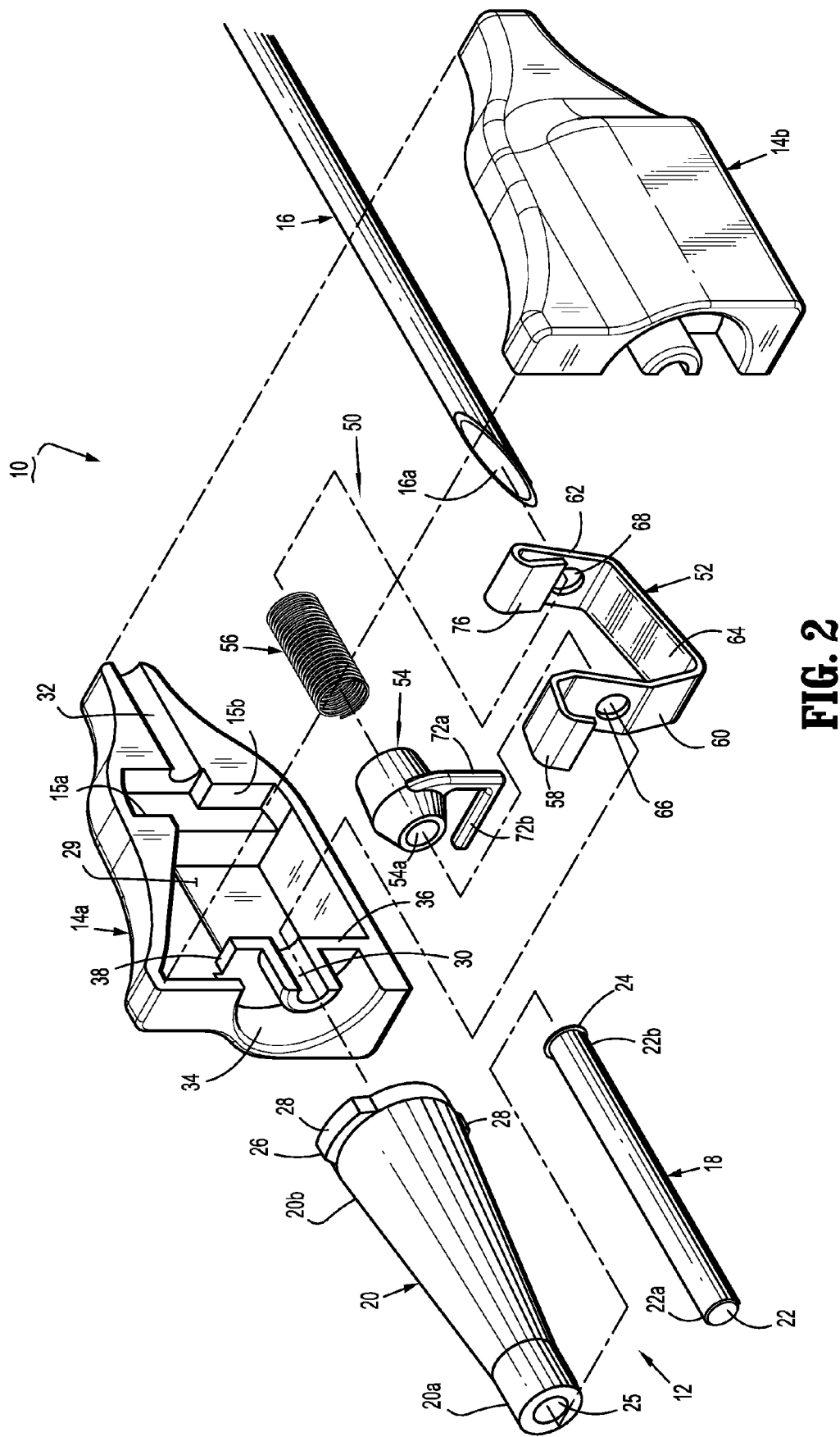
FIG. 2 is an exploded perspective view of the I.V. catheter assembly shown in FIG. 1.

Embodiments of a catheter assembly incorporating the presently disclosed locking clip assembly with spring-loaded collar will now be described in detail wherein like numerals designate identical or corresponding elements in each of the several views. In this description, the term proximal is generally used to indicate relative nearness of a referenced item to a user of the device and the term distal is used to indicate relative remoteness of a referenced item to a user of the device.

FIGS. 1-4 illustrate a catheter assembly 10 which incorporates one embodiment of the presently disclosed locking clip assembly 50. Catheter assembly 10 includes a cannula assembly 12, a locking clip assembly housing 14, an insertion needle 16 and locking clip assembly 50. Cannula assembly 12 includes a cannula 18 and a cannula hub 20. Cannula 18 and hub 20 may be constructed from metals or plastics. Cannula 18 defines a bore 22 and has an open distal end 22a and an open proximal end 22b. Proximal end 22b includes an annular flange 24 which is received in an annular slot 26 (FIG. 4) formed in a distal end 20a of cannula hub 20 to secure proximal end 22b of cannula 18 to distal end 20a of cannula hub 20. It is envisioned that a variety of known techniques can be used to secure cannula 18 to cannula hub 20, e.g., adhesives, welding, friction-fitting, etc. Cannula hub 20 defines a bore 25 which is in fluid communication with bore 22 of cannula 18. A proximal end 20b [FIG. 2 needs to be changed to read 20b] of cannula hub 20 includes a luer-type connector 26 which includes a pair of diametrically opposed tabs 28.

Housing 14 may also be formed from metals or plastics and includes housing half-sections 14a and 14b. Housing half-sections 14a and 14b define a chamber 29 dimensioned to receive locking clip assembly 50. Housing 14 defines forward and rearward openings 30 and 32 which are axially aligned and dimensioned to slidably receive insertion needle 16 and upper and lower bosses 15a and 15b which are positioned to interact with locking clip assembly 50 as will be discussed below. [see marked up FIG. 6] A forward end of housing 14 defines an annular recess 34 positioned about forward opening 30. Annular recess 34 is dimensioned to receive proximal end 20b of cannula hub 20. A partition wall 36 separates chamber 29 from annular recess 34. Partition wall 36 includes a cutout 38 which allows a portion of locking clip assembly 50 to extend from chamber 29 into annular recess 34 as will be discussed below.

Locking clip assembly 50 includes a locking clip 52, a collar 54 and a biasing member 56. Locking clip 52 has a distal hook-shaped end 58, a distal leg 60, a proximal leg 62 and an angled portion 64 interconnecting distal leg 60 to proximal leg 62. Distal leg 60 defines a trigger hole 66 which is dimensioned to slidably receive insertion needle 16. Proximal leg 62 defines a binding hole 68 which is dimensioned to slidably receive insertion needle 16 when locking clip 52 is in a first orientation and to bind with insertion needle 16 when locking clip 52 is in a second orientation. The proximal side of proximal leg 62 may include an uneven surface (not shown) which surrounds binding hole 68 to improve engagement with insertion needle 16 to further prevent proximal movement of insertion needle 16 through binding hole 68 when locking clip 52 is in its second orientation.

Collar 54 defines a longitudinal bore 54a including a step defining a shoulder 70 (FIG. 4). A cantilevered arm 72 having a vertical portion 72a and a horizontal portion 72b extends downwardly to a position beneath angled portion 64 of locking clip 52 (FIG. 4). Collar 54 is slidably positioned about insertion needle 16 between distal leg 60 of locking clip 52 and proximal leg 62 of locking clip. A biasing member 56 is positioned within stepped bore 54a of collar 54 such that one end of biasing member 56 engages shoulder 70 of stepped bore 54a and an opposite end of biasing member 56 engages a bent portion 76 of proximal leg 62 of locking clip 52.

When locking clip assembly 50 is assembled and positioned within chamber 29 of housing 14 with insertion needle 16 in its advanced position, a sharpened distal end 16a of insertion needle 16 extends from open distal end 22a of cannula 18. As discussed above, when insertion needle 16 is in its advanced position, needle 16 extends through housing 14, binding hole 68 of proximal leg 62 of locking clip 52, bore 54a of collar 54, trigger hole 66 of distal leg 60 of locking clip 52, bore 25 of cannula hub 20 and bore 22 of cannula 18. In this position, locking clip 52 is in a first orientation such that hook-shaped end 58 of locking clip 52 extends through cutout 38 of partition wall 36 and engages tab 28 of connector 26 to secure proximal end 20b of cannula hub 20 within annular recess 34 of housing 14.

Referring to FIGS. 3 and 4, in the first orientation of locking clip 52, collar 54 is positioned adjacent proximal leg 62 of locking clip 52 such that biasing member 56, e.g., a coil spring, is compressed to urge collar member 54 distally towards distal leg 60 of locking clip 52. Cantilevered arm 72 extends downwardly from collar 54 to a position in which horizontal portion 72b of arm 72 abuts angled portion 64 of locking clip 52. Engagement between arm 72 of collar 54, which is urged distally with collar 54 by biasing member 56, and angled portion 64 of locking clip 52 urges angled portion 64 of locking clip 52 upwardly within chamber 29 to urge locking clip 52 toward its second orientation. However, because needle 16 extends through both trigger hole 66 and binding hole 68, locking clip 52 cannot pivot upwardly and move to its second orientation. Thus, collar 54, including arm 72, are prevented from sliding distally about needle 16 and biasing member 56 remains compressed such that collar 54 is positioned adjacent to proximal leg 62 of locking clip 52.

Figure 5:
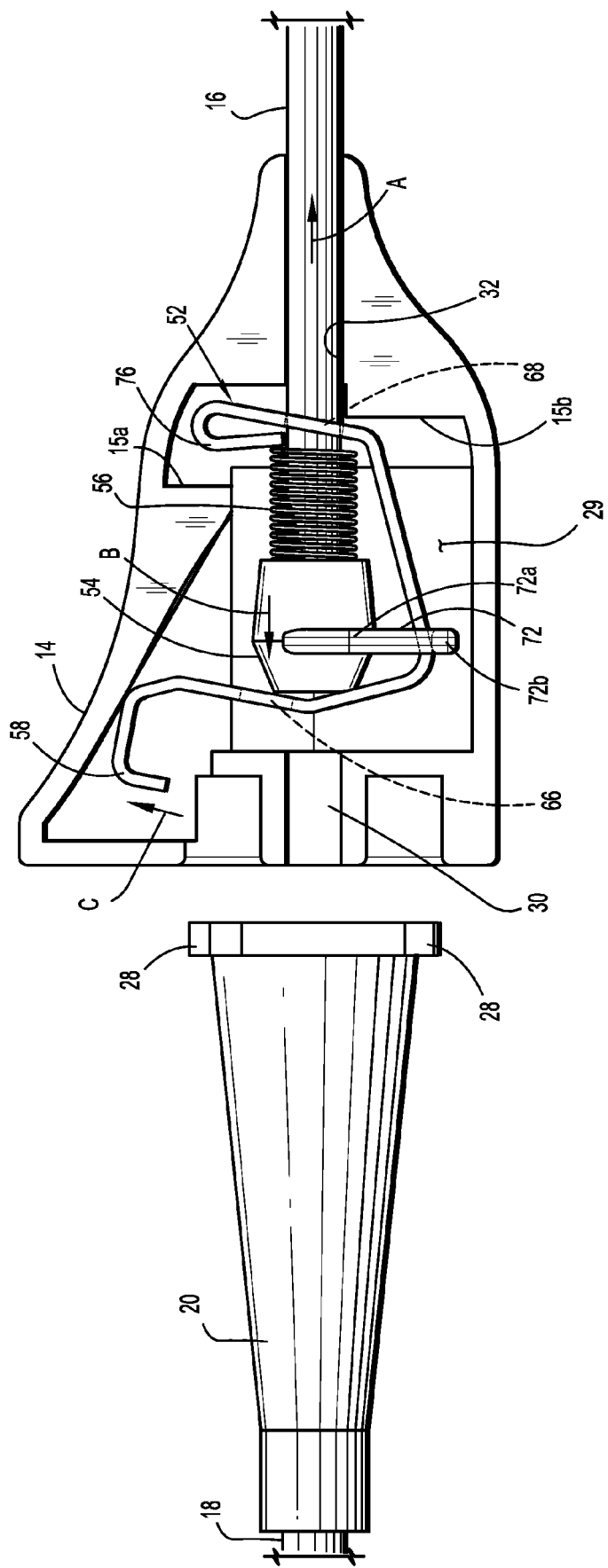
FIG. 5 is a side view of the I.V. catheter assembly shown in FIG. 3 with the insertion needle in a retracted position and the cannula assembly separated from the housing of the I.V. catheter assembly.
Figure 6:
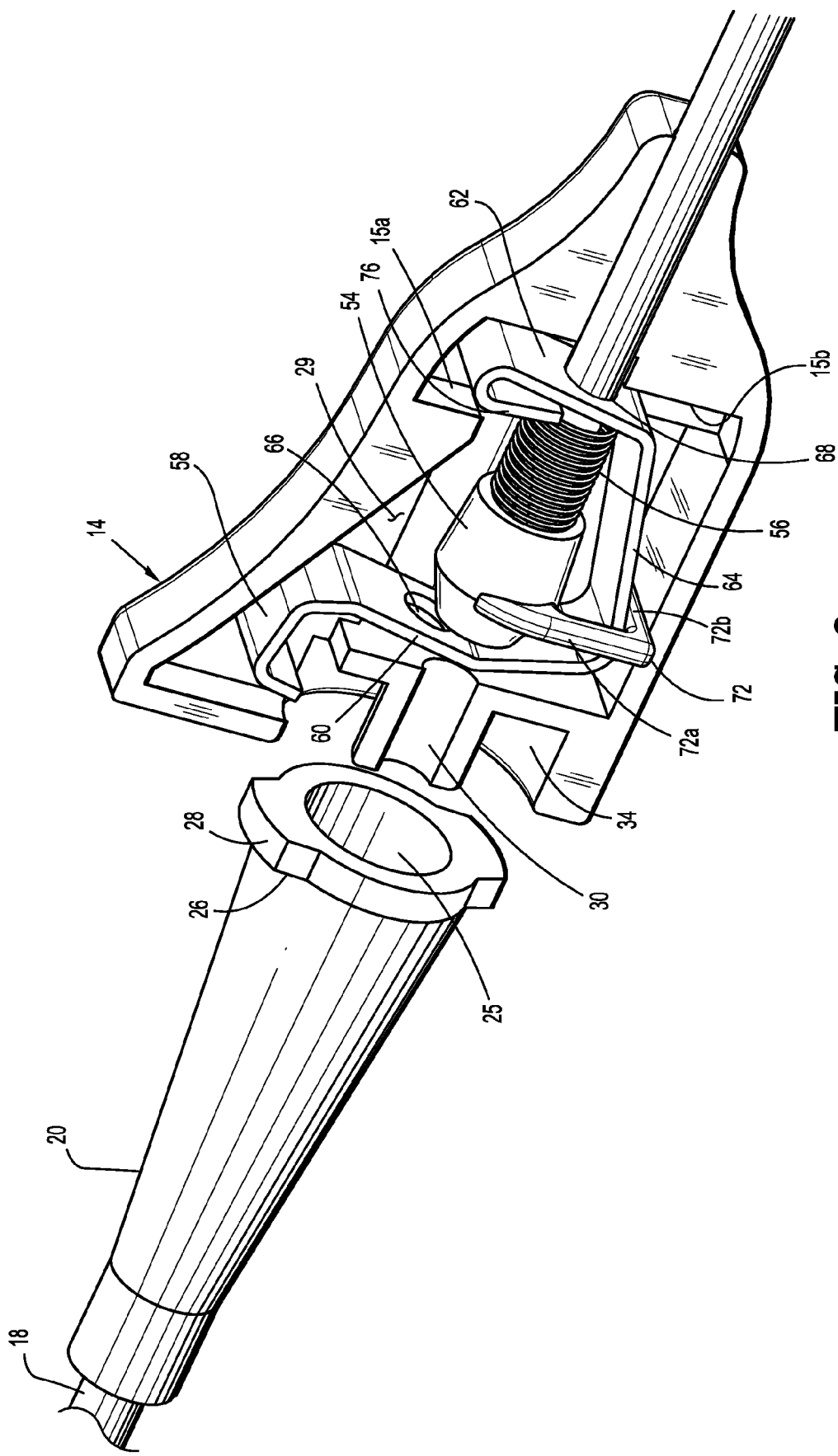
FIG. 6 is a side perspective view of the I.V. catheter assembly shown in FIG. 5 with the insertion needle in a retracted position and the cannula assembly separated from the housing of the I.V. catheter assembly.

Referring to FIGS. 5 and 6, when insertion needle 16 is moved in the direction indicated by arrow "A" in FIG. 5 from its advanced position (FIG. 3) to its retracted position (FIG. 5), insertion needle 16 is pulled through trigger hole 66 to disengage insertion needle 16 from distal leg 60 of locking clip 52. When this occurs, because biasing member 56 is in compression and is urging horizontal portion 72b of leg 72 distally into angled portion 64 of locking clip 52, locking clip 52 is pivoted upwardly in the direction indicated by arrow "C" in FIG. 5. As such, collar 54 and leg 72 are moved distally in the direction indicated by arrow "B" in FIG. 5 to pivot locking clip 52 to its second orientation. In its second orientation, hook shaped end 58 of locking clip 52 has pivoted out of engagement with tab 28 of cannula hub 20 to disengage cannula hub 20 from housing 14. Further, the orientation of binding hole 68 with respect to insertion needle 16 has changed such that the portion of locking clip 52 defining binding hole 68 binds with and prevents further retraction of insertion needle 16. When this occurs, the bottom portion of proximal side of proximal leg 62 of locking clip 52 contacts lower boss 15b of housing 14 to effect further binding. An attempt to move insertion needle 16 in the distal direction relative to housing 14 would result in the distal side of bent portion 76 of proximal leg 62 of locking clip 52 contacting upper boss 15a of housing 14 to also effect further binding. Thus, when locking clip 52 is in its second orientation, (FIG. 5) cannula hub 20 is disengaged from housing 14 and insertion needle 16 is prevented from being moved proximally and distally by engagement with the portion of locking clip 52 defining binding hole 68 (FIG. 6). Thus, the sharpened distal end 16a of insertion needle 16 is confined within housing 14 and can be safely disposed of without risking medical personnel to the risks associated with needle stick injuries.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A catheter assembly comprising:
   a cannula assembly including a cannula and a cannula hub;
      a locking clip assembly including a locking clip, a collar, and a biasing member, the locking clip having a first leg defining a trigger hole and a second leg defining a binding hole, the collar being positioned to engage the locking clip and the biasing member being positioned to urge the collar into engagement with the locking clip to urge the locking clip from a first orientation to a second orientation;
   a housing defining a chamber dimensioned to receive the locking clip assembly, the collar being moveable within the chamber of the housing to move the locking clip from the first orientation to the second orientation; and
   an insertion needle having a sharpened tip and being movable from an advanced position to a retracted position, wherein in the advanced position, the insertion needle extends through the housing, the binding and trigger holes of the locking clip and the cannula assembly such that a distal end of the insertion needle extends from a distal end of the cannula and the locking clip is retained in its first orientation, wherein in the retracted position, the distal end of the insertion needle is withdrawn through the cannula assembly and trigger hole of the locking clip such that, the collar and biasing member urge the locking clip to its second orientation within the housing, wherein in its second orientation, the binding hole binds with the insertion needle to prevent retraction of the insertion needle.

2. The catheter assembly of claim 1, wherein the biasing member includes a coil spring.

3. The catheter assembly of claim 1, wherein the collar defines a bore and is slidably positioned about the insertion needle.

4. The catheter assembly of claim 3, wherein the collar includes a cantilevered arm which is positioned to engage the locking clip.

5. The catheter assembly of claim 4, wherein the collar is slidably supported on the insertion needle between the first and second legs of the locking clip.

6. The catheter assembly of claim 5, wherein the biasing member is positioned between a proximal end of the collar and a distal surface of the second leg of the locking clip.

7. The catheter assembly of claim 6, wherein the locking clip has an angled portion interconnecting the first and second legs of the locking clip.

8. The catheter assembly of claim 7, wherein the collar includes an arm which engages the angled portion of the locking clip to urge the locking clip towards its second orientation.

9. The catheter assembly of claim 8, wherein the arm includes a vertical portion which extends downwardly from the collar and a horizontal portion which extends across the angled portion of the locking clip.

10. The catheter assembly of claim 1, wherein the housing defines an annular recess dimensioned to receive a proximal end of the cannula hub.

11. The catheter assembly of claim 10, wherein the proximal end of the cannula hub includes a coupling member.

12. The catheter assembly of claim 11, wherein the coupling member includes a luer-type connector having at least one radially extending tab.

13. The catheter assembly of claim 1, wherein the locking clip further includes a hook portion which is configured to engage the coupling member of the cannula hub when the locking clip is in its first orientation to releasably secure the cannula hub to the housing.

14. The catheter assembly according to claim 13, wherein the housing includes a partition wall separating the annular recess from the chamber, the partition wall defining a cutout dimensioned to receive the hook portion of the locking clip.

15. A locking clip assembly comprising:
   a housing defining a chamber and proximal and distal openings, the proximal and distal openings being dimensioned to receive an insertion needle of a catheter assembly;
   a locking clip having a first leg defining a trigger hole and a second leg defining a binding hole, the trigger hole and the binding hole being dimensioned to slidably receive an insertion needle of a catheter assembly, the locking clip being movably supported within the chamber of the housing from a first orientation to a second orientation;
   a collar movably positioned within the chamber of the housing to engage and move the locking clip from the first orientation to the second orientation; and
   a biasing member positioned to urge the collar into engagement with the locking clip to urge the locking clip from its first orientation to its second orientation;
   wherein in second orientation of the locking clip, the binding hole of the locking clip is positioned to bind with an insertion needle of a catheter assembly.

16. The locking clip assembly of claim 15, wherein the housing defines an annular recess dimensioned to receive a cannula hub of a catheter assembly.

17. The locking clip assembly of claim 15, wherein the locking clip further includes a hook portion configured to releasably engage a cannula hub of a catheter assembly.

18. The locking clip assembly of claim 15, wherein the locking clip further includes an angled portion interconnecting the first and second legs.

19. The locking clip assembly of claim 18, wherein the collar defines a bore dimensioned to slidably receive an insertion needle of a catheter assembly.

20. The locking clip assembly according to claim 19, wherein the collar includes an arm positioned to engage the angled portion of the locking clip.

21. The locking clip assembly of claim 20, wherein the collar is positioned between the first and second legs of the locking clip.

* * * * *